(12) United States Patent
Ordomskiy et al.

(10) Patent No.: US 8,921,635 B2
(45) Date of Patent: Dec. 30, 2014

(54) ONE-STEP METHOD FOR BUTADIENE PRODUCTION

(75) Inventors: Vitaly Valerievich Ordomskiy, Moscow (RU); Vitaly Leonidovich Sushkevich, Minsk (BY); Irina Igorevna Ivanova, Moscow (RU)

(73) Assignee: Obshchestvo S Ogranichennoy Otvetstvennostju "Unisit", Moscow (RU)

( * ) Notice: Subject to any disclaimer, the term of this patent is extended or adjusted under 35 U.S.C. 154(b) by 0 days.

(21) Appl. No.: 13/812,310

(22) PCT Filed: Jul. 27, 2011

(86) PCT No.: PCT/RU2011/000565
§ 371 (c)(1),
(2), (4) Date: Jan. 25, 2013

(87) PCT Pub. No.: WO2012/015340
PCT Pub. Date: Feb. 2, 2012

(65) Prior Publication Data
US 2013/0123554 A1 May 16, 2013

(30) Foreign Application Priority Data
Jul. 29, 2010 (RU) .................................. 2010131711

(51) Int. Cl.
*C07C 1/20* (2006.01)
*C07C 11/16* (2006.01)
*C07C 1/207* (2006.01)

(52) U.S. Cl.
CPC ............... *C07C 1/20* (2013.01); *C07C 2523/64* (2013.01); *C07C 2523/52* (2013.01); *C07C 2523/50* (2013.01); *C07C 2523/72* (2013.01); *C07C 2523/644* (2013.01); *C07C 2523/63* (2013.01); *C07C 11/16* (2013.01); *C07C 1/2072* (2013.01); *C07C 1/207* (2013.01)
USPC .......................................... 585/609; 585/607

(58) Field of Classification Search
CPC ................ C07C 1/2072–1/2076; C07C 11/16; C07C 1/207
USPC ................................................ 585/607, 609
See application file for complete search history.

(56) References Cited

U.S. PATENT DOCUMENTS

| | | | |
|---|---|---|---|
| 2,357,855 A | 9/1944 | Szukiewicz | |
| 2,374,433 A | 4/1945 | Ipatieff | |
| 2,403,743 A * | 7/1946 | Hitcheock et al. | 585/607 |
| 2,421,361 A * | 5/1947 | Toussaint et al. | 585/327 |
| 2,436,125 A | 2/1948 | Spence et al. | |
| 2,438,464 A * | 3/1948 | Spence et al. | 585/607 |
| 2,477,181 A | 7/1949 | Holman | |
| 2,548,883 A | 4/1951 | Harlow | |

FOREIGN PATENT DOCUMENTS

| | | |
|---|---|---|
| FR | 925617 | 9/1947 |
| GB | 573631 | 11/1945 |
| JP | 57102822 | 6/1982 |
| JP | 58059928 | 4/1983 |
| SU | 68428 | 1/1947 |

OTHER PUBLICATIONS

Ohnishi, Ryuichiro, Takao Akimoto, and Kozo Tanabe. "Pronounced Catalytic Activity and Selectivity of MgO-SiO2-Na2O for Synthesis of Buta-1,3-diene from Ethanol." Journal of the Chemical Society, Chemical Communications 22 (1985): 1613.*

Corson, B. B., H. E. Jones, C. E. Welling, J. A. Hinckley, and E. E. Stahly. "Butadiene from ethyl alcohol." Industrial and Engineering Chemistry 42 (1950): 359.*

Sheng, P.-Y., G.A. Bowmaker, and H. Idriss. "The Reactions of Ethanol over Au/CeO2." Applied Catalysis A: General 261.2 (2004): 171-81.*

Athina Nickitas-Etienne, International Preliminary Report on Patentability in PCT/RU2011/000565, Jan. 29, 2013, 5 pages, The International Bureau of WIPO, Geneva, Switzerland.

Paul O'Sullivan, International Search Report in PCT/RU2011/000565, Dec. 2, 2011, 2 pages, European Patent Office, Rijswijk, Netherlands.

Paul O'Sullivan, Written Opinion in PCT/RU2011/000565, Jan. 29, 2013, 4 pages, European Patent Office, Rijswijk, Netherlands.

* cited by examiner

*Primary Examiner* — In Suk Bullock
*Assistant Examiner* — Eric McCullough
(74) *Attorney, Agent, or Firm* — Florek & Endres PLLC

(57) ABSTRACT

This invention relates to gas-phase synthesis of butadiene from ethanol or ethanol and acetaldehyde mixture. The method of synthesis includes ethanol or ethanol and acetaldehyde mixture conversion in the presence of a catalyst, which differs from the known methods by the carrying out of the interaction in the presence of the solid catalyst, which contains metal, chosen from the group of silver, gold or copper, and metal oxide, chosen from the group of magnesium, titanium, zirconium, tantalum or niobium oxides. The method announced is used for condensation process under the conditions of continuous flow fixed bed reactor. The invention allows to reach high yield and selectivity to butadiene and high level of conversion of the feed.

16 Claims, No Drawings

ONE-STEP METHOD FOR BUTADIENE PRODUCTION

This application is a U.S. National Stage filing under 35 U.S.C. §371 of International Application No. PCT/RU2011/000565, filed Jul. 27, 2011, which in turn claims priority to Russian Patent Application No. 2010131711, filed Jul. 29, 2010.

FIELD OF THE INVENTION

This invention relates to the gas-phase method of butadiene production, particularly, to formation of butadiene from ethanol or from the mixture of ethanol and acetaldehyde.

PRIOR ART

Butadiene is essentially used as a monomer in the production of synthetic rubbers, such as butadiene rubber, butadiene-nitrile rubber, butadiene-styrene rubber etc.

At present two main methods for butadiene production are used in industry. In the first case, butadiene is obtained by catalytic dehydrogenation of n-butane and butylenes contained in refining and casing-head gases; this process is carried out in one or two steps. In the second case, butadiene is extracted from the products of oil pyrolysis. Because of the uplift in oil prices, alternative methods of obtaining butadiene are of major interest.

Traditional and well-known methods for butadiene production consist of two steps: ethanol dehydrogenation to acetaldehyde and further conversion of ethanol and acetaldehyde mixture into butadiene; catalysts based on copper chromite are used at the dehydrogenation step, while at the condensation tantalum or magnesium based oxide catalysts, deposited on silica, are used. Total conversion of ethanol and acetaldehyde in this process is about 35%, the butadiene yield from reacted ethanol and acetaldehyde is about 60%. The catalysts life time during the catalytic run is 15-30 hours, after which the catalysts need to be regenerated.

Methods, based on such heterogeneous catalytic systems, are described, for example, in the following patents: U.S. Pat. No. 2,438,464, U.S. Pat. No. 2,357,855, U.S. Pat. No. 2,477,181, JP 57102822, JP 58059928, GB 573631.

Also there is a method of butadiene production, in which zirconium and thorium oxides deposited on silica gel are used as a catalyst (U.S. Pat. No. 2,436,125 1948).

The closest analog of the method proposed is the one, which includes ethanol conversion on the catalyst, which contains magnesium oxide (U.S. Pat. No. 2,374,433 1945).

The disadvantages of known methods, including the prototype, are low butadiene yield, high reaction temperature, fast catalyst deactivation.

SUMMARY OF THE INVENTION

The aim of this invention is the development of one-step process, which allows to synthesize butadiene in milder conditions with high yield and high stability of catalyst activity in time.

The goal is reached by the described method of gas-phase synthesis of butadiene, in which ethanol or ethanol and acetaldehyde mixture are converted in the presence of solid catalyst, which contains metal, chosen from the group: silver, gold or copper, and metal oxide, chosen from the group: magnesium, titanium, zirconium or tantalum oxide.

It is possible to use the catalyst, in which oxides, chosen from the group of magnesium, titanium, zirconium or tantalum, are modified with alkali metals and/or cerium, tin or antimony oxides.

It is possible to use a catalyst, deposited on the support.

Preferably, process is carried out under gas-phase conditions at 200-400° C., under atmospheric pressure, with weight hourly space velocity (WHSV) in the range of 0.1-15 g/(g*h).

While carrying out the process with ethanol and acetaldehyde mixture, weight ratio of acetaldehyde to ethanol in mixture is (1-3):10, respectively.

Preferably, the process is carried out under the conditions of continuous flow in the fixed bed reactor.

The technical result of method realization as indicated in item 1 is high yield and selectivity of butadiene formation at high stability of catalytic activity in time. The result obtained is due to considerable decrease of highly active acetaldehyde content in the gas phase, as it is formed directly on the surface of the catalyst, which contains a metal with dehydrogenation function. This results in the decrease of the rate of deep condensation accompanied by formation of by-products and coke.

DESCRIPTION OF THE PREFERRED EMBODIMENTS

The realization of the method at given parameters leads to high yield and selectivity of butadiene production.

The proposed method of butadiene production comprises in general:

The catalyst pre-treatment includes heating in inert gas (nitrogen) flow up to 500° C. during 1 hour and calcination at this temperature during 30 minutes, then reactor is cooled down to the reaction temperature, the catalyst is reduced in hydrogen flow during 30 minutes and then the flow is switched to inert gas. Ethanol and acetaldehyde are fed into the continuous flow fixed bed reactor. At the reactor outlet the products obtained are divided in liquid and gas products. The products composition is analyzed by chromatographic method.

The conversion and the yield of target product are calculated as follows:

$$\text{Conversion}(\%) = n_{but}/(n_{acet.in.} + n_{ethan.in.}) \cdot 200;$$

$$\text{Yield}(\%) = n_{but}/(n_{acet.con.} + n_{ethan.con.}) \cdot 200;$$

where $n_{but}$—butadiene flow, mol/h;

$n_{acet.in.}$, $n_{ethan.in.}$—incoming flow of acetaldehyde and ethanol, mol/h;

$n_{acet.con.}$, $n_{ethan.con.}$—outcoming flow of converted acetaldehyde and ethanol, mol/h.

The examples, which illustrate the realization of the invention and achievement of the technical result in comparison with known methods of butadiene production, are listed below.

Example 1

Catalyst, which composition is $1Ag$-$10ZrO_2$-$500SiO_2$, and which has silica as a support, is placed in the continuous flow reactor, purged with nitrogen at 500° C. during 1 hour, then the temperature is decreased to 325° C. and the catalyst is blown off with hydrogen during 30 minutes. Then it is switched to nitrogen flow (10 ml/min) and ethanol is supplied at a rate of 1.2 g/h. The reaction is carried out during 3 hours. The conversion of ethanol at the reactor outlet is 34%, the yield of butadiene per converted ethanol is 72%.

The unreacted ethanol is directed to recycle. The results are presented in Table 1.

Example 2

The process is carried out as in Example 1. The difference is that the measurement of process parameters is carried out in 45 hours after the beginning of the reaction. The results are presented in Table 1.

Example 3 (Comparative)

The process is carried out as in Example 1. The difference is that the catalyst used is magnesium oxide (as in the prototype U.S. Pat. No. 2,374,433), deposited on silica gel. The results are presented in Table 1.

Example 4 (Comparative)

The process is carried out as in Example 3. The difference is that the measurement of process parameters is carried out in 45 hours after the beginning of the reaction. The results are presented in Table 1.

Example 5 (Comparative)

The process is carried out as in Example 1. The difference is that the catalyst used is based on zirconium oxide, deposited on silica gel (analog-U.S. Pat. No. 2,436,125) (The catalyst is obtained by silica gel impregnation with zirconile nitrate). The results are presented in Table 1.

The analysis of the results, obtained in Examples 1-5, shows the benefits of the proposed method of butadiene production from ethanol in comparison with known methods. As follows from the examples, known catalysts do not allow to reach high conversion and yield of butadiene. On the contrary, application of the catalysts containing announced oxides and dehydrogenating metal allows to reach high conversion and yield of butadiene.

Further, in the examples, the possibility of the processes realization over different catalysts from the group announced under different process conditions is shown.

Example 6

The process is carried out as in Example 1. The difference is that the catalyst contains copper instead of silver, and process is carried out with the addition of acetaldehyde with acetaldehyde/ethanol ratio 1:10. The results are presented in Table 1.

Example 7

The process is carried out as in Example 6. The difference is that the catalyst contains gold instead of copper. The results are presented in Table 1.

Example 8

The process is carried out as in Example 1. The difference is that magnesium oxide is used instead of zirconium oxide, and the process is carried out with the addition of acetaldehyde with acetaldehyde/ethanol ratio 1:10. The results are presented in Table 1.

Example 9

The process is carried out as in Example 8. The difference is that titanium oxide is used instead of magnesium oxide. The results are presented in Table 1.

Example 10

The process is carried out as in Example 8. The difference is that tantalum oxide is used instead of magnesium oxide. The results are presented in Table 1.

Example 11

The process is carried out as in Example 8. The difference is that niobium oxide is used instead of magnesium oxide. The results are presented in Table 1.

Example 12

The process is carried out as in Example 1. The difference is that the catalyst contains tin oxide in addition The composition of the used catalyst is $1Ag-10ZrO_2-3SnO_2-500SiO_2$. The process is carried out with the addition of acetaldehyde with acetaldehyde/ethanol ratio 1:10. The results are presented in Table 1.

Example 13

The process is carried out as in Example 12. The difference is that antimony oxide is added instead of tin oxide. The results are presented in Table 1.

Example 14

The process is carried out as in Example 12. The difference is that catalyst contains cerium oxide instead of tin oxide. The results are presented in Table 1.

Example 15

The process is carried out as in Example 1. The difference is that the composition of the used catalyst is $1Ag-10ZrO_2-3Na_2O-500SiO_2$. The process is carried out with the addition of acetaldehyde with acetaldehyde/ethanol ratio 1:10. The results are presented in Table 1.

Examples 12-15 illustrate a possibility to use in the butadiene process solid catalysts with modifying additives announced.

Example 16

The process is carried out as in Example 14. The difference is that aluminum oxide is used instead of silica as a support. The results are presented in Table 1.

Example 17

The process is carried out as in Example 14. The difference is that aluminosilicate is used instead of silica gel as a supporter. The results are presented in Table 1.

Example 18

The process is carried out as in Example 14. The difference is that the catalyst is used without support. The results are presented in Table 1.

Example 19

The process is carried out as in Example 14. The difference is that the reaction temperature is 200° C. The results are presented in Table 1.

Example 20

The process is carried out as in Example 14. The difference is that the reaction temperature is 400° C. The results are presented in Table 1.

Example 21

The process is carried out as in Example 14. The difference is that acetaldehyde/ethanol ratio is 3:10. The results are presented in Table 1.

Example 22

The process is carried out as in Example 14. The difference is that weight hourly space velocity is 0.1 g/g·h. The results are presented in Table 1.

Example 23

The process is carried out as in Example 14. The difference is that the weight hourly space velocity is 15 g/g·h. The results are presented in Table 1.

Examples 19-23 illustrate a possibility to realize the method of butadiene production in a broad range of process parameters' variation.

Hereby, the examples given prove the possibility of realization of one-step butadiene production process with the achievement of the technical result announced, which is high level of conversion, high yield of butadiene and high catalyst stability with time on stream.

INDUSTRIAL APPLICABILITY

The invention can be used in chemical industry, in particular for manufacture of butadiene which can be further used in production of synthetic rubbers, such as butadiene rubber, butadiene-nitrile rubber, butadiene-styrene rubber etc.

TABLE 1

| Example No | Catalyst composition (mole) | Temperature, ° C. | WHSV, g/g·h | Acetaldehyde/ethanol | Time on stream, h | Conversion, % | Butadiene yield per converted reactants, mol. % |
|---|---|---|---|---|---|---|---|
| 1 | $1Ag—10ZrO_2—500SiO_2$ | 325 | 0.3 | 0 | 3 | 34 | 72 |
| 2 | $1Ag—10ZrO_2—500SiO_2$ | 325 | 0.3 | 0 | 45 | 32 | 71 |
| 3 | $1MgO—4SiO_2$ | 325 | 0.3 | 0 | 3 | 18 | 40 |
| 4 | $1MgO—4SiO_2$ | 325 | 0.3 | 0 | 45 | 11 | 37 |
| 5 | $1ZrO_2—4SiO_2$ | 325 | 0.3 | 0 | 3 | 8 | 48 |
| 6 | $1Cu—10ZrO_2—500SiO_2$ | 325 | 0.3 | 1/10 | 3 | 45 | 71 |
| 7 | $1Au—10ZrO_2—500SiO_2$ | 325 | 0.3 | 1/10 | 3 | 31 | 82 |
| 8 | $1Ag—10MgO—500SiO_2$ | 325 | 0.3 | 1/10 | 3 | 45 | 64 |
| 9 | $1Ag—10TiO_2—500SiO_2$ | 325 | 0.3 | 1/10 | 3 | 35 | 72 |
| 10 | $1Ag—10Ta_2O_5—500SiO_2$ | 325 | 0.3 | 1/10 | 3 | 33 | 71 |
| 11 | $1Ag—10Nb_2O_5—500SiO_2$ | 325 | 0.3 | 1/10 | 3 | 28 | 69 |
| 12 | $1Ag—10ZrO_2—3SnO_2—500SiO_2$ | 325 | 0.3 | 1/10 | 3 | 36 | 75 |
| 13 | $1Ag—10ZrO_2—3SbO_2—500SiO_2$ | 325 | 0.3 | 1/10 | 3 | 38 | 76 |
| 14 | $1Ag—10ZrO_2—3CeO_2—500SiO_2$ | 325 | 0.3 | 1/10 | 3 | 41 | 81 |
| 15 | $1Ag—10ZrO_2—3Na_2O—500SiO_2$ | 325 | 0.3 | 1/10 | 3 | 42 | 72 |
| 16 | $1Ag—10ZrO_2—3CeO_2—500Al_2O_3$ | 325 | 0.3 | 1/10 | 3 | 32 | 57 |
| 17 | $1Ag—10ZrO_2—3CeO_2—20Al_2O_3—500SiO_2$ | 325 | 0.3 | 1/10 | 3 | 34 | 74 |
| 18 | $1Ag—10ZrO_2—3CeO_2$ | 325 | 0.3 | 1/10 | 3 | 41 | 56 |
| 19 | $1Ag—10ZrO_2—3CeO_2—500SiO_2$ | 200 | 0.3 | 1/10 | 3 | 6 | 60 |
| 20 | $1Ag—10ZrO_2—3CeO_2—500SiO_2$ | 400 | 0.3 | 1/10 | 3 | 64 | 41 |
| 21 | $1Ag—10ZrO_2—3CeO_2—500SiO_2$ | 325 | 0.3 | 3/10 | 3 | 44 | 68 |
| 22 | $1Ag—10ZrO_2—3CeO_2—500SiO_2$ | 325 | 0.1 | 1/10 | 3 | 44 | 78 |
| 23 | $1Ag—10ZrO_2—3CeO_2—500SiO_2$ | 325 | 15 | 1/10 | 3 | 12 | 67 |

The invention claimed is:

1. A one-step method for producing butadiene comprising the step of converting ethanol or ethanol/acetaldehyde mixture in the presence of a solid catalyst, wherein the solid catalyst comprises a metal and a metal oxide,
   wherein the metal is selected from the group consisting of silver, gold, copper, and combinations thereof,
   and wherein the metal oxide is selected from the group consisting of magnesium oxide, titanium oxide, zirconium oxide, tantalum oxide, niobium oxide, and combinations thereof.

2. The method according to claim 1, wherein the solid catalyst further comprises an additive elected from the group consisting of alkali metals, cerium oxide, tin oxide, antimony oxide, and combinations thereof.

3. The method according to claim 1, wherein the metal and metal oxide of the solid catalyst are deposited on a support selected from the group consisting of silica, alumina, aluminosilicate and combinations thereof.

4. The method according to claim 1, wherein the converting step is carried out at 200-400° C.

5. The method according to claim 1, wherein the weight ratio of acetaldehyde to ethanol is from 0:10 to 3:10.

6. The method according to claim 1, wherein the converting step is carried out under the conditions of continuous flow fixed bed reactor.

7. The method of claim 5, wherein the weight ratio of acetaldehyde to ethanol is from 1:10 to 3:10.

8. The method of claim 7, wherein the weight ratio of acetaldehyde to ethanol is 1:10 or 3:10.

9. The method of claim 1, wherein the converting step is carried out under atmospheric pressure.

10. The method of claim 1, wherein the converting step is carried out at weight hourly space velocity of 0.1-15 g/g*h.

11. The method of claim 10, wherein the conversion of ethanol is at least 12%.

12. The method of claim 1, wherein the yield of butadiene per converted ethanol is at least 41%.

13. The method of claim 1, wherein unconverted ethanol is recycled.

14. The method of claim 1, wherein a support for the catalyst is not present.

15. The method according to claim 1, wherein the solid catalyst is activated by a process comprising:
   a. heating the catalyst up to 500° C. in inert gas;
   b. cooling the catalyst to the reaction temperature in inert gas; and
   c. reducing the catalyst in a hydrogen flow.

16. The method of claim 1, wherein the solid catalyst further comprises an additive from the group of alkali metal consisting of sodium, potassium, cesium compounds and combinations thereof.

* * * * *